United States Patent [19]

Ishimori

[11] Patent Number: 5,080,833
[45] Date of Patent: Jan. 14, 1992

[54] IMMOBILIZATION OF BIOACTIVE SUBSTANCE ON LIPID COMPOSITION CONTAINING MODIFIED LIPID COMPOUND

[75] Inventor: Yoshio Ishimori, Tokyo, Japan

[73] Assignee: Kabushiki Kaisha Toshiba, Kawasaki, Japan

[21] Appl. No.: 246,092

[22] Filed: Sep. 19, 1988

[30] Foreign Application Priority Data

Sep. 21, 1987 [JP] Japan .................................. 62-234777
Sep. 22, 1987 [JP] Japan .................................. 62-237780
Mar. 16, 1988 [JP] Japan .................................. 63-62264

[51] Int. Cl.$^5$ .................. A23J 7/00; G01N 33/543; G01N 33/92; C12Q 1/00
[52] U.S. Cl. .................................. 260/408; 260/404; 260/405; 260/403; 435/4; 436/71; 436/518
[58] Field of Search ................. 435/4, 7; 436/71, 828, 436/824, 513, 811, 518, 524; 260/403, 404, 405, 408

[56] References Cited

U.S. PATENT DOCUMENTS 3,564,099  2/1971  Marco ................................ 426/635
4,480,041 10/1984  Myles et al. .
4,544,545 10/1985  Ryan et al. .

FOREIGN PATENT DOCUMENTS 0144084  6/1985  European Pat. Off. .
62-214357  9/1987  Japan .

Primary Examiner—Robert A. Wax
Assistant Examiner—David R. Preston
Attorney, Agent, or Firm—Oblon, Spivak, McClelland, Maier & Neustadt

[57] ABSTRACT

A lipid represented by the following formula (I) can react with and immobilize a bioactive substance at functional group $-Y-(CH_2)_n-X$:

$$R-Y-(CH_2)n-X \qquad (I)$$

wherein X is a halogen atom, Y is $-NHCO-$, $-COO-$, or $-O-$, R is a lipid residue, n is an integer from 1 to 6. In order to immobilize a bioactive substance to this lipid, an SH group is preferably introduced to the bioactive substance. A liposome reagent comprising a liposome including a bioactive substance-immobilized composition containing at least the above lipids, a bioactive substance immobilized on the surface of the liposome, and a marker substance enclosed in the liposome does not cause a nonspecific reaction in a protein-containing sample such as blood or serum and hence is stable upon immunoassay. Therefore, with this liposome reagent, immunoassay can be performed with high accuracy and sensitivity.

10 Claims, 7 Drawing Sheets

IMMOBILIZATION OF BIOACTIVE SUBSTANCE ON LIPID COMPOSITION CONTAINING MODIFIED LIPID COMPOUND

BACKGROUND OF THE INVENTION

1. Field of the Invention

The present invention relates to a lipid compound modified by a functional group which can be suitably bonded to bioactive substances such as an antigen, an antibody, and an enzyme.

2. Description of the Related Art

The present invention further relates to a lipid composition, containing at least the above lipid compound, and suitable for immobilization of bioactive substances.

The present invention still further relates to a method for immobilizing bioactive substances to the above lipid composition and the lipid composition having the bioactive substances immobilized thereto by this method.

The present invention still further relates to a liposome reagent obtained by immobilizing an antigen or antibody on the surface of a liposome prepared from the above lipid composition. This liposome reagent is effective in immunoassay.

Immunoassay is an analysis method of identifying and quantifying a specific antigen or antibody contained in a sample by utilizing high specificity and sensitivity of an antigen-antibody reaction.

Known examples of a quantitative analysis method according to immunoassay are radioimmunoassay (to be referred to as RIA hereinafter) and immunoelectrophoresis. However, in RIA, since a radioactive element is used, special equipment for dealing with the radioactive element must be used, and an operator having a license for this purpose must operate the equipment. In addition, it is difficult to handle RIA waste material because a radioactive element is used.

Meanwhile, since the sensitivity is low in immunoelectrophoresis, immunoelectrophoresis cannot be applied when the concentration of a target substance is significantly low. In addition, a long time period is required for measurement.

Recently, immunoassay has been performed using a lipid membrane such as a liposome or an LB membrane on the surface of which an antigen or antibody is immobilized, and then introducing a complement. In this immunoassay, the complement is activated by an antigenantibody reaction between the immobilized antigen or antibody and a target substance in a sample, and lysis of the lipid membrane is finally resulted by a cascade reaction of the activated complement. As a reagent for performing immunoassay utilizing such a reaction of a complement, the present inventors have disclosed, in, e.g., Japanese Patent Disclosure (Kokai) No. 60-117159, a liposome reagent on the surface of which a hydrophilic antigen or antibody is immobilized and in which a hydrophilic marker substance is enclosed. This liposome reagent is destroyed by the above reaction in a sample in which an antigen or antibody is present, and the marker substance enclosed therein is released. The amount of the released marker substance can be correlated with that of the target substance. Therefore, the target substance can be quantified by quantifying the released marker substance by a predetermined analysis method (e.g., fluorescent analysis).

In another conventional method, an LB membrane on the surface of which an antigen or antibody is immobilized is used, and a target substance in a sample solution is quantified by an antigen-antibody reaction and a reaction of a complement in the same manner as when the liposome reagent is used.

Furthermore, analysis other than immunoassay can be performed by immobilizing a bioactive substance other than an antigen or antibody, e.g., an enzyme to a lipid membrane such as a liposome or lipid bilayer (LB) membrane.

Conventional methods of immobilizing the bioactive substances such as an enzyme and an antibody on the surface of a lipid membrane are as follows:

a method of using phosphatidyl ethanolamine (DTP-DPPE) modified by N-hydroxysuccinimidyl-3-(2-pyridyldithio)propionate (SPDP) (e.g., L.D. Leserman, J. Barnet, F. Kourilski and J.N. Weinstein; Nature, 288, PP. 602–604 (1980), and F.J. Martin, W.L. Hubbell and D. Papahadjopoulos; Biochemistry, 20, PP. 4229–4238 (1981));

a method of using a lipid to which a thiomaleimide group is introduced (H. Hashimoto, M. Sugawara and H. Endoh; J. Immunol. Methods, 62, PP. 155–162 (1983)); and a method of using a lipid to which a disulfide group is introduced (Japanese Patent Publication No. 61-45775).

However, the above immobilizing methods have the following problems. That is, in these methods, when immunoassay is performed using a lipid membrane to which an antigen or antibody is immobilized, the lipid membrane is sometimes destroyed when it is mixed with blood or serum regardless of whether a target substance is present. For example, the liposome reagent (disclosed in Japanese Patent Disclosure (Kokai) No. 60-117159) having an antibody immobilized on the surface thereof is significantly destroyed when it is just mixed with blood or serum as a sample, and release of an enclosed substance is found. For this reason, it is impossible to accurately quantify the target substance in the blood because background noise is high. Such a problem is assumed to be caused since a nonspecific reaction occurs between another protein or minor chemical component in the blood or serum and the liposome in addition to the antigen-antibody reaction between the target substance and the liposome.

In order to eliminate such adverse effects of the nonspecific reaction, a serum or protein-containing sample is diluted by, e.g., about 100 times. In this method, however, a target substance which is originally contained at only a low concentration is further diluted before analysis. Therefore, it is sometimes very difficult to precisely quantify the target substance of certain types.

SUMMARY OF THE INVENTION

It is, therefore, a first object of the present invention to provide a lipid compound to which bioactive substances can be suitably immobilized. More specifically, the invention intends to provide a lipid compound which can be used as a means for immobilizing an antigen or antibody on the surface of a lipid membrane such as a liposome comprising the lipid compound, the obtained liposome reagent or the like for immunoassay being free from non specific reaction.

The lipid compound according to the present invention is represented by the following formula (I) wherein X is a halogen atom, Y is —NHCO—, —COO—, or —O—, R is a lipid residue, and n is an integer from 1 to 6:

$$R-Y-(CH_2)_n-X \ldots \qquad (I)$$

The lipid represented by formula (I) reacts with a bioactive substance at functional group $-Y-(CH_2)_n-X$ and can be bonded to the bioactive substance.

It is a second object of the present invention to provide a lipid composition suitable for immobilizing bioactive substances and, more specifically, a lipid composition which can be used to manufacture a lipid membrane having an antigen or antibody immobilized thereto, such as a liposome reagent for immunoassay. The obtained liposome reagent is stable and free from a nonspecific reaction in a sample.

This lipid composition contains at least the above lipid compound according to the present invention and may contain another lipid. With this lipid composition, a lipid membrane such as a liposome or LB membrane or another lipid-formed body can be easily obtained. Since a functional group of the lipid compound is present on the surface of the membrane, the bioactive substances can be immobilized through the functional group. When an antigen or antibody is immobilized, a composition for immunoassay which does not cause a nonspecific reaction in a sample solution such as blood or serum can be obtained, for example, in the form of a membrane.

It is a third object of the present invention to provide a method for suitably immobilizing bioactive substances to the lipid composition, and a lipid composition to which bioactive substances are immobilized by this method. In this method, the bioactive substances are immobilized to the lipid composition by mixing the bioactive substances having an SH group introduced thereto with the composition under proper conditions. With this method, functional group $-Y-(CH_2)_n-X$ of the composition reacts with the SH group introduced in the bioactive substances so that the bioactive substances are stably immobilized through a thioether bond ($-S-C-$).

It is a fourth object of the present invention to provide a liposome reagent which can be used as an immunoassay reagent. This liposome reagent consists of a liposome consisting of the lipid composition, an antigen or antibody immobilized on the surface of the liposome, and a marker substance enclosed in the liposome. As compared with a conventional liposome reagent, according to the liposome reagent of the present invention, the frequency of nonspecific reaction occurring in a sample solution such as blood or serum is significantly small. Therefore, with this liposome reagent, immunoassay can be performed with high accuracy and sensitivity.

DETAILED DESCRIPTION OF THE PREFERRED EMBODIMENTS

A lipid compound of the present invention is represented by the following formula (I) wherein X is a halogen atom, Y is $-NHCO-$, $-COO-$, or $-O-$, R is a lipid residue, and n is an integer from 1 to 6:

$$R-Y-(CH_2)_n-X \ldots \qquad (I)$$

As described above, lipid compound (I) is a modified lipid having a halogenated alkyl group introduced through Y. In this case, Y is preferably $-NHCO-$.

Lipid compound (I) in which Y is $-NHCO-$ can be obtained by, for example, reacting an amino group-containing lipid with halogenated carboxylic acid under proper conditions to cause dehydration condensation, thereby forming a peptide bond therebetween.

Although any amino group-containing lipid can be used as long as it contains an amino group, a preferable example is a phospholipid or glycolipid containing an amino group. Preferable examples of the amino group-containing phospholpid are dipalmitoylphophatidyl ethanolamine, cytidyl phosphoglyceride, dioleoylphosphatidyl ethanolamine, dilauroylphosphatidyl ethanolamine, palmitoyl-stearoyl-glycerophospho ethanolamine, glycerophosphono ethylamine, and ceramide phosphoethanolamine. Examples of the amino group-containing glycolipid are neuraminoyl glyceride, muramoyl glyceride, and glucosaminoyl glyceride.

The halogenated carboxylic acid used in the above reaction is obtained by halogenating a carboxylic acid having 2 to 7 carbon atoms and, preferably, is a halogenated acetic acid. In this case, a halogen atom is preferably Cl, Br, or I.

The above reaction is preferably performed in the presence of a catalyst such as N-hydroxysuccinimide, dicyclohexylcarbodiimide, and triethylamine.

Lipid compound (I) in which Y is —COO— can be obtained by, for example, reacting a hydroxyl group-containing lipid with a halogenated carboxylic acid under proper conditions, thereby forming an ester bond therebetween.

Examples of the hydroxyl group-containing lipids are glycerol phosphoglyceride, phosphatidyl inositol, and sulfolipid I.

Lipid compound (I) in which Y is —O— can be obtained by, for example, reacting one of the hydroxyl group-containing lipids enumerated above with halohydrincarboxylic acid under proper conditions to cause a dehydration reaction, thereby forming an ether bond therebetween.

The lipid represented by formula (I) can be reacted with and bonded to a bioactive substance at a portion of functional group $-Y-(CH_2)_n-X$. A reactive portion of the bioactive substance is a nucleophilic functional group such as $-NH_2-$ and $-SH$ present on its surface. When the lipid compound and the bioactive substance are mixed and reacted with each other under proper conditions, X in the lipid compound is substituted with the nucleophilic functional group of the bioactive substance so that the bioactive substance is bonded to the lipid compound.

In this case, the functional group at the bioactive substance side is preferably —SH. This is because the nucleophilic property of —SH is larger than those of other functional groups. For example, a monoclonal antibody cannot be bonded without the —SH group.

If the bioactive substance does not have the —SH group, the —SH group can be obtained by modifying the bioactive substance with SPDP and reducing its —S—S— bond. An immunoglobulin such as a monoclonal antibody may be used as an F(ab')fragment having the —SH group by reducing the —S—S—bond at a hinge portion.

Lipid compound (I) can be used together with other lipids as a lipid composition for immobilizing bioactive substances. Examples of the lipid other than that represented by formula (I) are cholesterol and dipalmitoylphosphatidyl choline. This lipid composition can be used in the form of a lipid bilayer membrane such as a liposome or LB membrane. In this case, the stability of the liposome or LB membrane can be improved by adding cholesterol. In addition, a liposome including cholesterol and dipalmitoylphosphatidyl choline has an excellent long-time preservation stability, compared to a liposome including other unsaturated or saturated fatty acid. The content of the lipid represented by formula (I) in this lipid composition is preferably 0.1 to 10 mol%.

A bioactive substance can be immobilized to the lipid composition by a bonding reaction between lipid compound (I) contained in the composition and the bioactive substance. Examples of the bioactive substance to be immobilized are a protein or peptide (e.g., an immunoglobulin such as IgG, IgE, IgD, IgA, and IgM; an enzyme such as transaminase, lactate dehydrogenase, and creatine phosphokinase; a tumor marker such as AFP and CEA; a peptide hormone such as insulin and growth hormone), a glucide (e.g., various Lewis antigens, Forssman antigens, and microorganism cell wall polysaccharides), a nucleic acid related substance (e.g., polynucleotide, nucleotide, and nucleoside), a lipid (e.g., lipoprotein and cardiolipin), and other low-molecular weight substances (e.g., coenzyme, steroid hormone, thyroxin, and various drugs).

In order to prepare the lipid composition of the present invention into the form of a liposome, a conventional liposome preparation method can be used. For example, the lipid composition is dissolved into a solvent and then the solvent is removed, thereby preparing a thin membrane of the composition. Then, a solution (e.g., an aqueous solution) using a solvent which cannot dissolve the lipid composition is added and shaken to prepare the liposome.

In order to prepare the composition in the form of a lipid bilayer membrane, a conventional lipid bilayer preparation method can be used. For example, by using the Langmuir-Blodgett technique, the composition is developed on a water surface to form a monomolecular membrane, and the formed monomolecular membrane is placed on a holder, thereby preparing the lipid bilayer membrane.

The lipid composition of the present invention is effective in the field of immunoassay. That is, a liposome reagent effective in immunoassay can be prepared from the lipid composition. This liposome reagent consists of a liposome prepared using the lipid composition, a bioactive substance (in this case, an antigen or antibody) immobilized on the surface of the liposome, and a marker substance enclosed in the liposome. The antigen or antibody is selected from the bioactive substances described above. Examples of the marker substance used in the liposome reagent are a fluorescent compound such as carboxyfluorescein, an absorptive compound such as rhodamine B, and a luminous compound such as luminol.

The liposome reagent can be prepared as follows.

First, a liposome is prepared from the lipid composition of the present invention by the above method. At this time, a liposome in which a marker substance is enclosed can be obtained using an aqueous solution of the marker substance as the solution using a solvent which can not dissolve the lipid composition. Meanwhile, an antigen or antibody having a functional group such as $-NH_2$ or $-SH$ is prepared. The antigen or antibody is added to a suspension of the liposome and then mixed and reacted with each other under proper conditions. As a result, the antigen or antibody is reacted with the functional group $(-Y-(CH_2)_n-X)$ present on the surface of the liposome and bonded to and immobilized on the liposome surface. If the functional group introduced to the antigen or antibody is —SH, the antigen or antibody is stably immobilized on the liposome through a thioether bond (—S—C—).

The liposome having the antigen or antibody immobilized thereon, i.e. liposome reagent, can specifically react with the antigen or antibody in a sample and therefore can be used in immunoassay. For this reason, a reaction of immobilizing the antigen or antibody is called sensitizing. The efficiency of sensitizing is not 100% and is generally not so high. Therefore, even in the liposome reagent subjected to sensitizing, a free functional group (in this invention, $-Y-(CH_2)_n-X$) which is not bonded to the antigen or antibody still remains. In a conventional liposome reagent, it is assumed that this free functional group causes a nonspecific reaction based on the activation of complement through the alternative path way. Similarly, in the present invention, some functional groups (—Y—(CH$_2$)$_n$—X) remain free in the liposome after sensitizing. However, such a functional group is hydrolyzed under a proper pH condition (a pH of 8 to 11) and converted into —Y—(CH$_2$)$_n$—OH. After conversion, an action of the functional group for causing the nonspecific reaction is significantly low. Therefore, by using the liposome reagent of the present invention, the nonspecific reaction can be eliminated to perform immunoassay with high accuracy.

Note that sensitizing is preferably performed under the condition of a pH of 7 to 11 when the —SH group is introduced in the antigen or antibody. If the pH is less than 7, the efficiency of sensitizing is not sufficient. If the pH exceeds 11, the liposome on which the bioactive substance is immobilized is unstable. In this condition, for example, the liposome is destroyed in blood or serum.

When a liposome reagent sensitized by a specific antibody is to be used, immunoassay is performed as follows. That is, the liposome reagent is added to a sample containing a target substance (antigen) and reacted for a predetermined time, thereby causing an antigen-antibody reaction. Then, suitable amounts of a second antibody against the target substance is added together with suitable amount of a complement and reacted for a predetermined time. In this case, not only an isolated and refined complement but also a body fluid such as guinea pig serum having a high complement concentration may be used as a complement source. Then, the amount of the marker substance released from the liposome, which is destroyed by an effect of the complement, is measured by a suitable means. Since the released marker substance can be correlated with the target substance in the sample, the target substance can be quantified by quantifying the released marker substance. In actual quantification, on the basis of a calibration curve formed in advance using a target substance of a known concentration, the amount of the target substance is determined in accordance with a measurement value of the marker substance measured under the same conditions as those of calibration curve formation.

A time required for causing a sufficient reaction between the liposome reagent of the present invention and the target substance differs in accordance with the type of target substance, the characteristics of the liposome, and the reaction conditions, and in accordance with the type, purity, and bonding form of the bioactive substance which constitutes the liposome reagent. For this reason, a pretest is preferably conducted using a sample containing the same substance as the target substance and prepared to obtain a known concentration, thereby setting an optimal reaction time for the liposome reagent and the target substance.

Examples of the target substance which can be quantified by immunoassay using the liposome reagent are a tumor marker (e.g., AFP, BFP, CEA, and POA), an immunoglobulin (e.g., IgG, IgE, IgD, IgA, and IgM), a hormone (e.g., insulin and T$_3$), and drugs. The range of the target substances is wide.

Figures 1, 2:
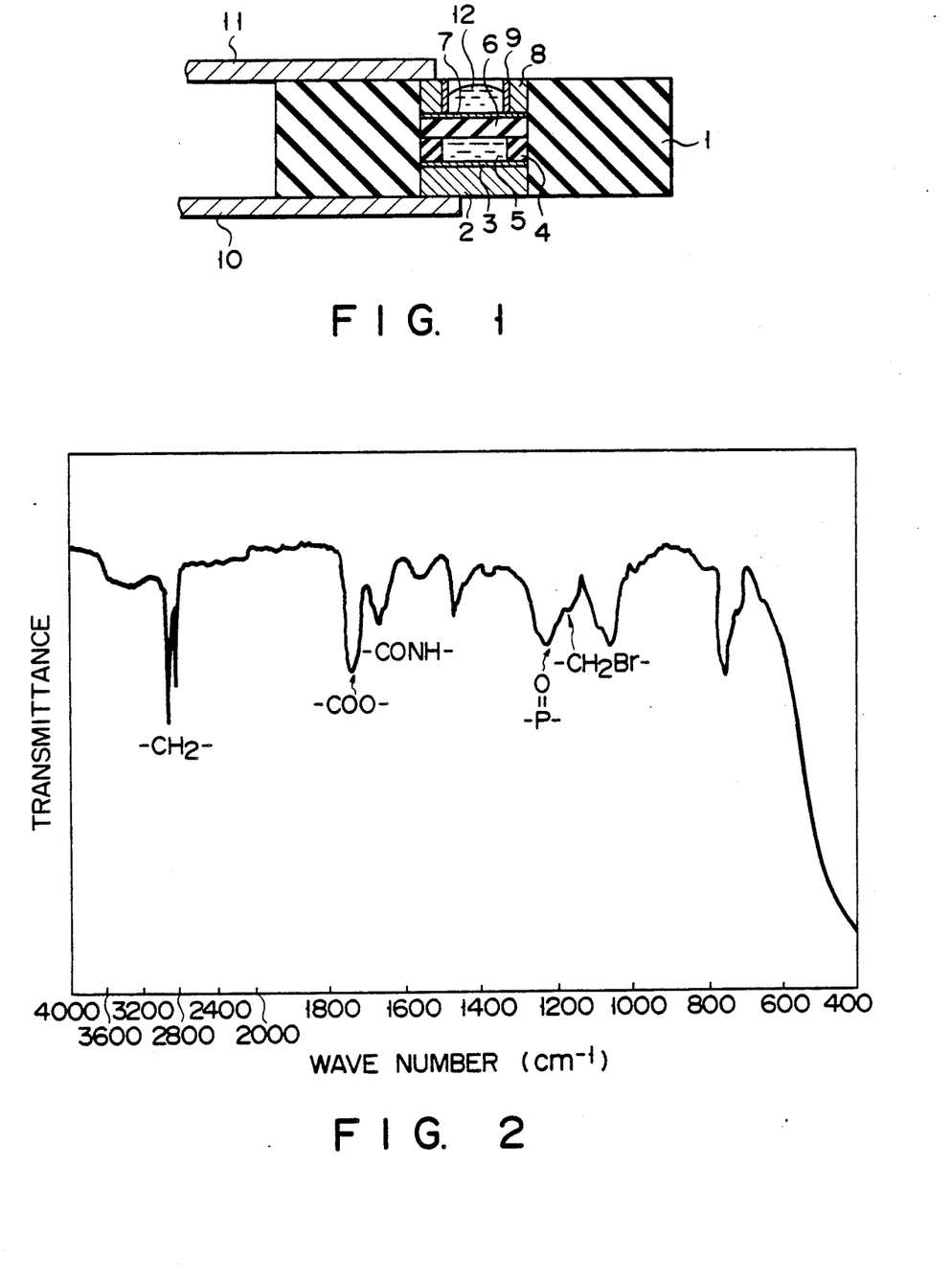
FIG. 1 is a sectional view showing an embodiment of an immunoassay apparatus using an LB membrane, prepared from a lipid according to the present invention, and having a bioactive substance immobilized on the surface thereof.
FIG. 2 is a graph showing an infrared absorption spectrum of BrAc-DPPE prepared in Example 1 of the present invention.

The lipid composition for immobilizing the bioactive substances according to the present invention can be used in the form of an LB membrane. For example, FIG. 1 shows an immunoassay apparatus utilizing an LB membrane having an antibody immobilized thereon. In FIG. 1, resin holder 1 has a through hole at its central portion. Disk-like silver electrode 2 having Ag/AgCl electrode 3 on its upper surface, annular ceramic spacer 4, ceramic filter 6 having LB membrane 7 to which an antibody has been immobilized on its upper surface, and annular silver electrode 8 having Ag/AgCl electrode 9 on its inner surface are sequentially stacked from a bottom portion in the through hole of holder 1. Saline 5 is filled in a hollow portion on electrode 3. Saline 5 is in contact with the lower surface of membrane 7 through the pores of filter 6. Measurement terminals 10 and 11 are connected to electrodes 3 and 8, respectively. Note that a DC power source and a resistance meter (neither of which are shown) are connected to terminals 10 and 11. Reference numeral 12 denotes a sample solution containing a target substance.

This apparatus utilizes an antigen-antibody reaction between the target substance in solution 12 and the bioactive substance immobilized on membrane 7, and an accompanied reaction in which a large number of pores are formed in membrane 7 by an effect of a separately added complement. When a large number of pores are formed in membrane 7, an electrolyte vigorously flows, and the membrane resistance of membrane 7 measured between terminals 10 and 11 is reduced. The amount of the target substance in the sample solution can be correlated with the number of pores, and the number of pores can be correlated with changes in membrane resistance. Therefore, the target substance in the sample solution can be quantified by measuring changes in membrane resistance.

Examples of the present invention will be described in detail below.

Example 1

(1) Preparation of Bromoacetyldipalmitoylphosphatidyl Ethanolamine (BrAc-DPPE)

Figure 3:
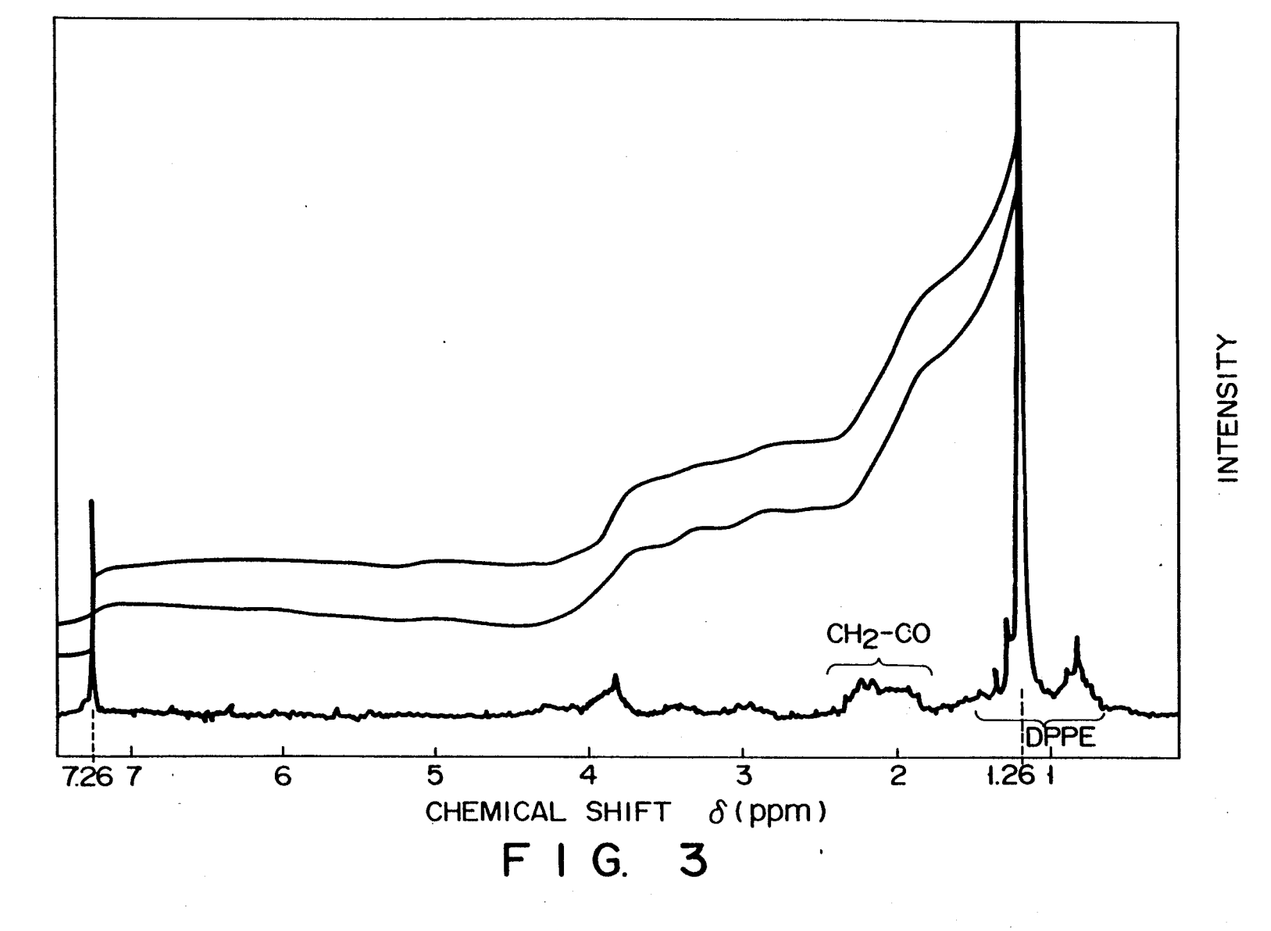
FIG. 3 is a graph showing a $^1$H-NMR spectrum of the BrAc-DPPE prepared in Example 1 of the present invention.

70 mg of dipalmitoylphosphatidyl ethanolamine (DPPE) available from Sigma Inc., 25 mg of bromoacetic acid available from Wako Pure Chemicals Inc., and 20 mg of hydroxysuccinimide available from Peptide Institute Co., Ltd. were suspended in about 30 ml of chloroform. After 30 mg of dicyclohexylcarbodiimide available from Peptide Institute Co., Ltd. and 40 μl of triethylamine available from Wako Pure Chemicals Inc. were added to the resultant solution, the solution was reacted at room temperature overnight. After the solvent was removed from the obtained solution, 30 ml of ethyl acetate were added. The obtained white precipitate was filtered and then the solvent was removed again. The resultant material was dissolved in 2 ml of chloroform, and the product was separated by a thin layer chromatography #5717 (trade name) available from Merck Schuchardt using a solvent mixture of chloroform/ methanol/water=65/25/4 as a developing solvent. An infrared absorption spectrum of the obtained BrAc-DPPE is shown in FIG. 2, and its $^1$H-NMR spectrum is shown in FIG. 3. In FIG. 2, various characteristic absorptions appear in addition to characteristic absorption at 1170 cm$^{-1}$ caused by —CH$_2$Br. In FIG. 3, a peak indicating a proton of CH$_2$—CO is found in addition to peaks indicating DPPE. It was confirmed that the product had the following formula by comparing these spectrums with spectrums of a material (DPPE).

The BrAc-DPPE was diluted to be 1 mM and preserved at $-20°$ C.

(2) Preparation of BrAc-DPPE-containing Liposome

All the lipids used were dissolved in chloroform or a chloroform/methanol (2/1) solvent mixture.

200 μl of 5 mM dipalmitoylphosphatidyl choline (DPPC) available from Sigma Inc., 100 μl of 10 mM cholesterol available from Sigma Inc., and 50 μl of 1 mM BrAc-DPPE were placed in a pear shape flask having a volume of 10 ml. After 2 ml of chloroform were added, the solution was mixed well. Then, the solvent was removed using a rotary evaporator in a water bath at a temperature of about 40° C. To the resultant residue, 2 ml of chloroform were added. Then, the mixture was sufficiently agitated, and the solvent was removed again using the rotary evaporator. By repeating this treatment several times, a thin lipid membrane was formed on the flask wall surface. The flask was placed in a desiccator and evacuated by a vacuum pump for about an hour to completely remove the solvent.

Then, 100 μl of 0.2 M carboxyfluorescein (Eastman Kodak Inc., pH =7.4: to be referred to as CF hereinafter) were added and the interior of the flask was replaced with nitrogen. Continuously, the flask was sealed and dipped in a water bath at about 60° C. for about a minute. Thereafter, the flask was vigorously shaken by a Vortex mixer until the thin lipid membrane on the flask wall surface completely disappeared. As a result, a liposome suspension was prepared. A small amount of 0.01 M HEPES buffer (containing 0.85% of NaCl, pH=7.45: to be referred to as HBS hereinafter) was added to the liposome suspension, and then all the resultant material was transferred to a centrifuge tube and repeatedly centrifuged at 4° C. and 15000 rpm for 20 minutes. The obtained liposome was suspended in 2 ml of HBS.

(3) Reaction between BrAc-DPPE-containing Liposome and Guinea Pig Serum

The BrAc-DPPE-containing liposome prepared in (2) was diluted by a factor of 10 by a gelatin veronal buffer (GVB+, pH=7.2). Meanwhile, a guinea pig serum was diluted by the GVB+ at predetermined dilution rates between factors of 1 to 80. Equal amounts of these materials were mixed and maintained at 37° C., and the fluorescence intensity of the CF released after 30 minutes was measured by fluorospectrophotometer MTP-32 (trade name) available from Corona Electronic Co., Ltd. with an excitation wavelength of 490 nm and a fluorescence wavelength of 530 nm.

The relative release rate of the marker substance was calculated on the basis of the above measurement and in accordance with the following equation:

Relative release rate (%)=$(Fe-Fo)/(Fa-Fo)$ where Fe is the measured fluorescence intensity, Fo is the fluorescence intensity obtained when the GVB+ was added (in this case, the liposome was not destroyed at all), and Fa is the fluorescence intensity obtained when deionized water was added to completely destroy the liposome. Note that fluorescence intensities of $10^{-7}$ and $10^{-8}$ M CF solutions were used as standard values.

Figure 4:
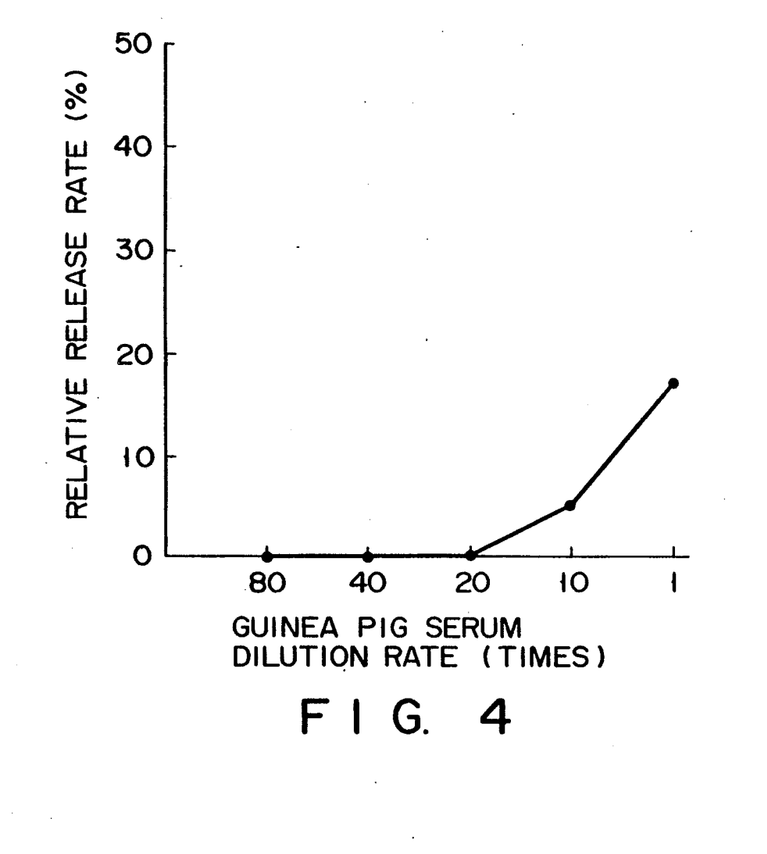
FIG. 4 is a graph showing a relative release rate of a CF obtained when a BrAc-DPPE-containing liposome prepared in Example 1 of the present invention is mixed with a guinea pig serum solution at various states of dilution up to 80 fold (times)

Results are shown in FIG. 4. As is apparent from FIG. 4, the liposome was more or less destroyed when the serum solution having a dilution rate of a factor of 10 or less was added, but the liposome was not destroyed at all when the serum solution having a dilution rate of a factor of 20 or more was added.

(4) Immobilization of Human IgG to BrAc-DPPE-containing Liposome

The BrAc-DPPE-containing liposome prepared in (3) was suspended in 1 ml of a 3 mg/ml human IgG/HBS solution and then the suspension was mixed and agitated at 20° C. for 43 hours in order to cause the immobilization reaction. After the reaction, the resultant material was subjected to centrifugal washing by three times with GVB$^-$ (GVB+ not containing $Ca^{2+}$ and $Mg^{2+}$). Finally, 2 ml of the GVB$^-$ were added and the mixture was preserved in a refrigerator.

Figure 5:
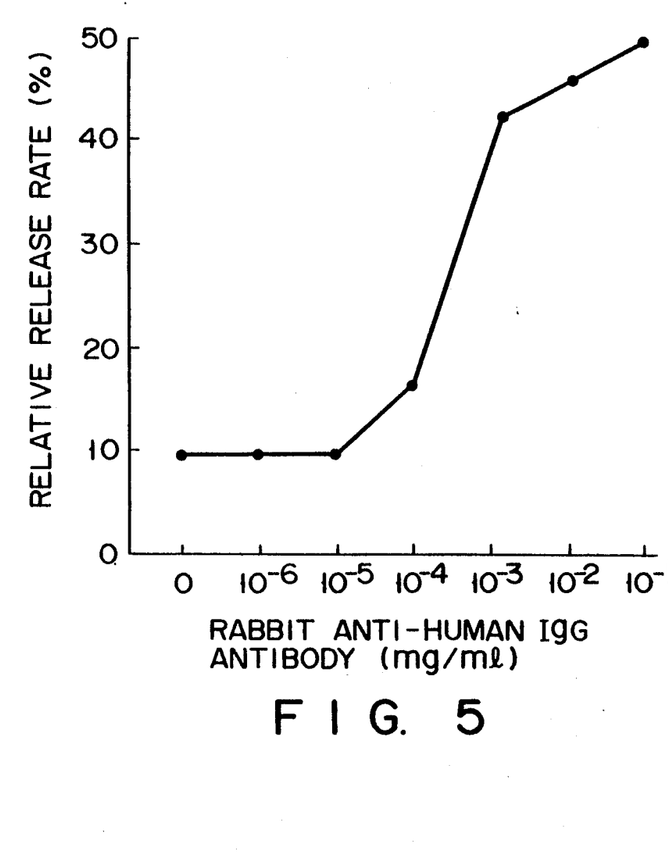
FIG. 5 is a graph showing a relative release rate of the CF obtained when a human IgG-immobilized BrAc-DPPE-containing liposome is mixed with a rabbit anti-human IgG antibody solution.

(5) Measurement of Rabbit Anti-Human IgG Antibody by Human IgG-immobilized Liposome The human IgG-immobilized liposome obtained in (4) was diluted by a factor of 10 with the GVB+. Meanwhile, a rabbit anti-human IgG antibody was diluted to predetermined concentrations between $10^{-6}$ to $10^{-1}$ mg/ml with the GVB+. Equal amounts of these materials were mixed and reacted at 37° C., and a fluorescence intensity of the CF released after 30 minutes was measured by the fluorospectrophotometer. A relative release rate was similarly obtained as described above on the basis of measurement results. Results are shown in FIG. 5. Note that in FIG. 5, 0 on the abscissa represents an addition of a solution obtained by diluting guinea pig serum with the GVB+ by a factor of 40. As is apparent from FIG. 5, a response depending on the concentration of the rabbit anti-human IgG antibody can be obtained by the human IgG-immobilized BrAc-DPPE-containing liposome, and therefore measurement can be performed with high accuracy.

REFERENCE EXAMPLE 1

Figure 6:
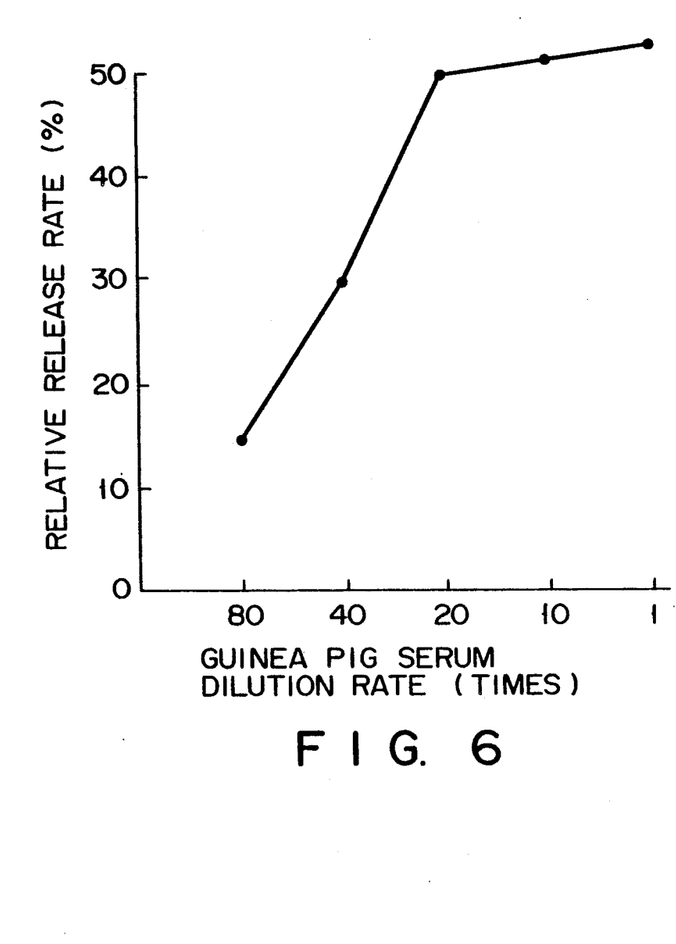
FIG. 6 is a graph showing a relative release rate of the CF obtained when a DTP-DPPE-containing liposome prepared in Reference Example 1 is mixed with a guinea pig serum solution.

Reaction between Liposome Containing DTP-DPPE (Conventional Immobilizing Reagent) and Guinea Pig Serum DTP-DPPE is DPPE derivative having dithiopyridylpropionic acid amide introduced thereto. DPPE and N-succinimidyl-3-(2-pyridyldithio)propionate (SPDP) were reacted with each other in the presence of triethylamine to prepare DTP-DPPE. A DTP-DPPE-containing liposome was prepared following the same procedures as in Example 1 except that the DTP-DPPE was used instead of BrAc-DPPE. Then, the DTP-DPPE-containing liposome was mixed with guinea pig serum to obtain a relative release rate of the CF following the same procedures as in Example 1. Results are shown in FIG. 6. As is apparent from FIG. 6, the DTP-DPPE-containing liposome was destroyed even by guinea pig serum having a high dilution rate and hence was very unstable.

REFERENCE EXAMPLE 2

Reaction between Liposome Containing MPB-DPPE (Conventional Immobilizing Reagent) and Guinea Pig Serum MPB-DPPE is DPPE derivative having Maleimidophenylbutylate (MPB) introduced thereto.

Figure 7:
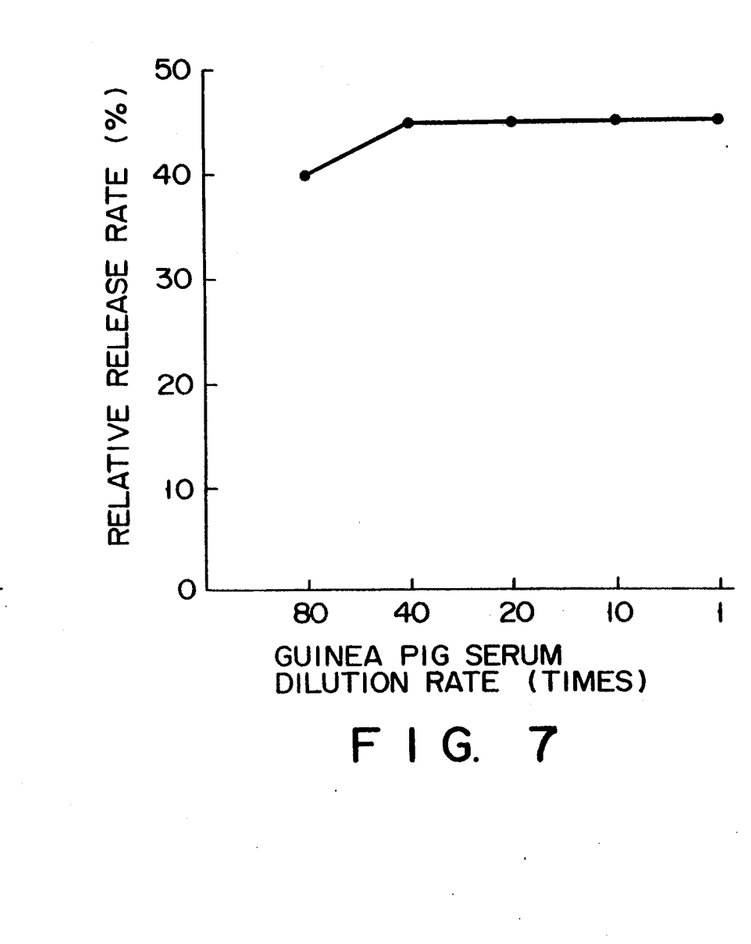
FIG. 7 is a graph showing a relative release rate of the CF obtained when an MPB-DPPE-containing liposome prepared in Reference Example 2 is mixed with a guinea pig serum solution.

In accordance with a method by Hashimoto et al., DPPE and succinimidyl-4-(p-maleimidophenyl)butylate (SMPB) available from Pierce Co., were reacted with each other in the presence of dicyclohexylcarbodiimide and triethylamine to prepare MPB-DPPE. An MPB-DPPE-containing liposome was prepared following the same procedures as in Example 1 except that the MPB-DPPE was used instead of the BrAc-DPPE. Then, the MPB-DPPE-containing liposome was mixed with guinea pig serum to obtain a relative release rate of the CF following the same procedures as in Example 1. Results are shown in FIG. 7. As is apparent from FIG. 7, the MPB-DPPE-containing liposome was destroyed even by guinea pig serum having a high dilution rate and hence was very unstable.

EXAMPLE 2

(1) Preparation of Functional Lipid (ClAc-DPPE, BrAc-DPPE, and IAc-DPPE)

1 millimole of halogenated acetic acid (chloroacetic acid, bromoacetic acid, and iodoacetic acid were independently used) was dissolved in 30 ml of chloroform. After 1.2 millimole of N-hydroxysuccinimide and 1.2 millimole of dicyclohexylcarbodiimide were added to the resultant solution, the solution was reacted at room temperature for three hours. Thereafter, the resultant material was dried by a rotary evaporator, and 30 ml of ethyl acetate were added. After the produced white precipitate was filtered, the solvent was removed again, and the resultant material was dissolved in 10 ml of chloroform again. Then, 100 micromoles of DPPE were suspended in 30 ml of chloroform, 2 ml of the above solution and 50 μl of triethylamine were added thereto, and the resultant solution was reacted at room temperature overnight. Thereafter, the solvent was condensed, and the product was separated and refined by a thin layer chromatography using a solvent mixture of chloroform/methanol=70/30 as a developing solvent. The yield of the DPPE to which a halogenated acetyl group was introduced was about 50%. A final product was diluted to a concentration of 1 mM by chloroform and preserved at −20° C.

(2) Preparation of Liposome

Following the same procedures as in Example 1, a liposome (in which the CF was enclosed as a marker substance) containing the DPPE to which the halogenated acetyl group was introduced was prepared.

(3) Modification of Monoclonal Antibody 10 mg of a monoclonal anti-human α-fetoprotein (AFP) antibody were dissolved in an acetic acid buffer of pH 3.5, 100 μg of pepsin were added, and the mixture was reacted at 37° C. for an hour. Thereafter, only an F(ab')$_2$ fraction was fractionated by a high-performance liquid chromatography. The F(ab')$_2$ fraction was dissolved in a 0.1 M phosphate buffered saline (pH6), 10 mg of mercaptoethylamine hydrochloride were added, and the mixture was reacted at 37° C. for 90 minutes. Thereafter, the resultant material was subjected to gel filtration performed by Sephadex G-25 (trade name) available from Pharmasia Fine Chemicals Inc. using a 0.01 M borate buffered saline (pH 8.0) as a developing solvent, thereby fractionating only a protein fraction (Fab'). OD 280 nm of this Fab' fraction was about 1. The Fab' fraction contained a free SH group.

(4) Immobilization of Monoclonal Antibody to Liposome

The liposome suspension prepared in (2) and the Fab' fraction obtained in (3) were mixed and reacted under stirring at 20° C. for 44 hours. After the reaction, the resultant material was washed three times by the GVB−, and finally suspended in 2 ml of the GVB− and stored at 4° C.

Figure 8:
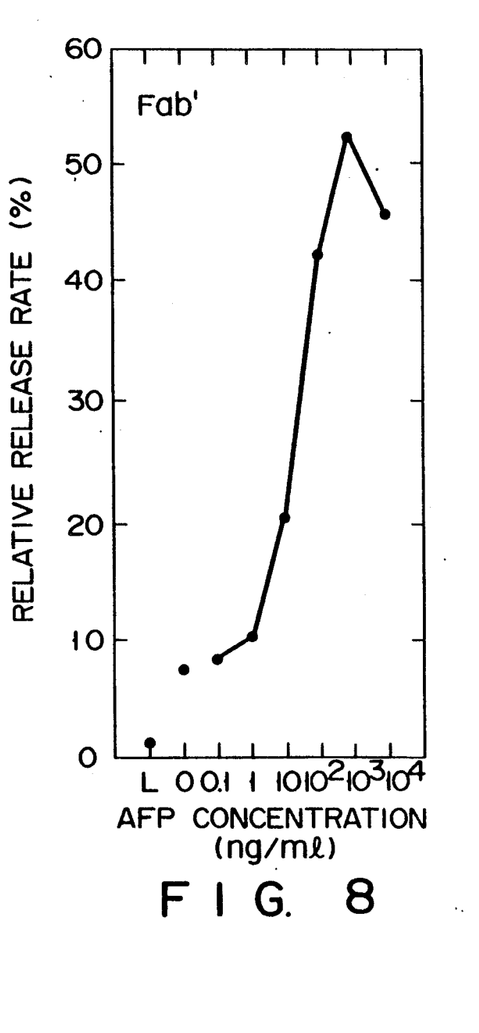
FIG. 8 is a graph showing a relative release rate of the CF obtained when a monoclonal antibody-immobilized BrAc-DPPE-containing liposome prepared in Example 2 of the present invention is mixed with a human AFP solution.

(5) Measurement of Human AFP by Using Monoclonal Antibody-Immobilized Liposome The monoclonal antibody-immobilized liposome prepared in (4) was diluted by a factor of 10 by adding the GVB+, thereby obtaining liposome suspension. Meanwhile, a human AFP was diluted by adding the GVB+, thereby obtaining human AFP solutions each of which had a predetermined concentration. The concentrations of the human AFP solutions fell within the range of 0.1 to $10^4$ ng/ml and were different from each other. 10 μl of the liposome suspension and the human AFP solution of each concentration were mixed and incubated at 37° C. for 10 minutes. 25 μl of a rabbit anti-human AFP antibody (Dako Inc.) solution diluted by a factor of 50 and 25 μl of a complement (guinea pig serum) solution diluted by a factor of 20 were added to the resultant solution and the mixture was reacted at 37° C. for 30 minutes. Then, the reaction was stopped by 100 μl of a 0.01 M EDTA-veronal buffer, and the released CF amount in each case of the human AFP solutions was measured following the same procedures as in Example 1. Results are shown in FIG. 8. In this measurement, BrAc-DPPE was used as a functional lipid. Note that in FIG. 8, L on the abscissa represents a use of the liposome suspension only, and 0 thereon represents an addition of the GVB+ instead of AFP. As is apparent from FIG. 8, according to this monoclonal antibody-immobilized liposome, the human AFP can be measured with very high accuracy within the concentration range of 1 to $10^3$ ng/ml.

(6) Effect of Type of Halogen in Functional Lipid

Following the same procedures as in (3), an Fab' fraction of a monoclonal anti-human AFP antibody was fractionated, and its concentration was adjusted to be as half as the above concentration, i.e., OD 280 nm=0.5. Thereafter, following the same procedures as in (4), ClAc-DPPE, BrAc-DPPE, and IAc-DPPE were reacted with the resultant solution to prepare a monoclonal antibody-immobilized liposome.

Figure 9:
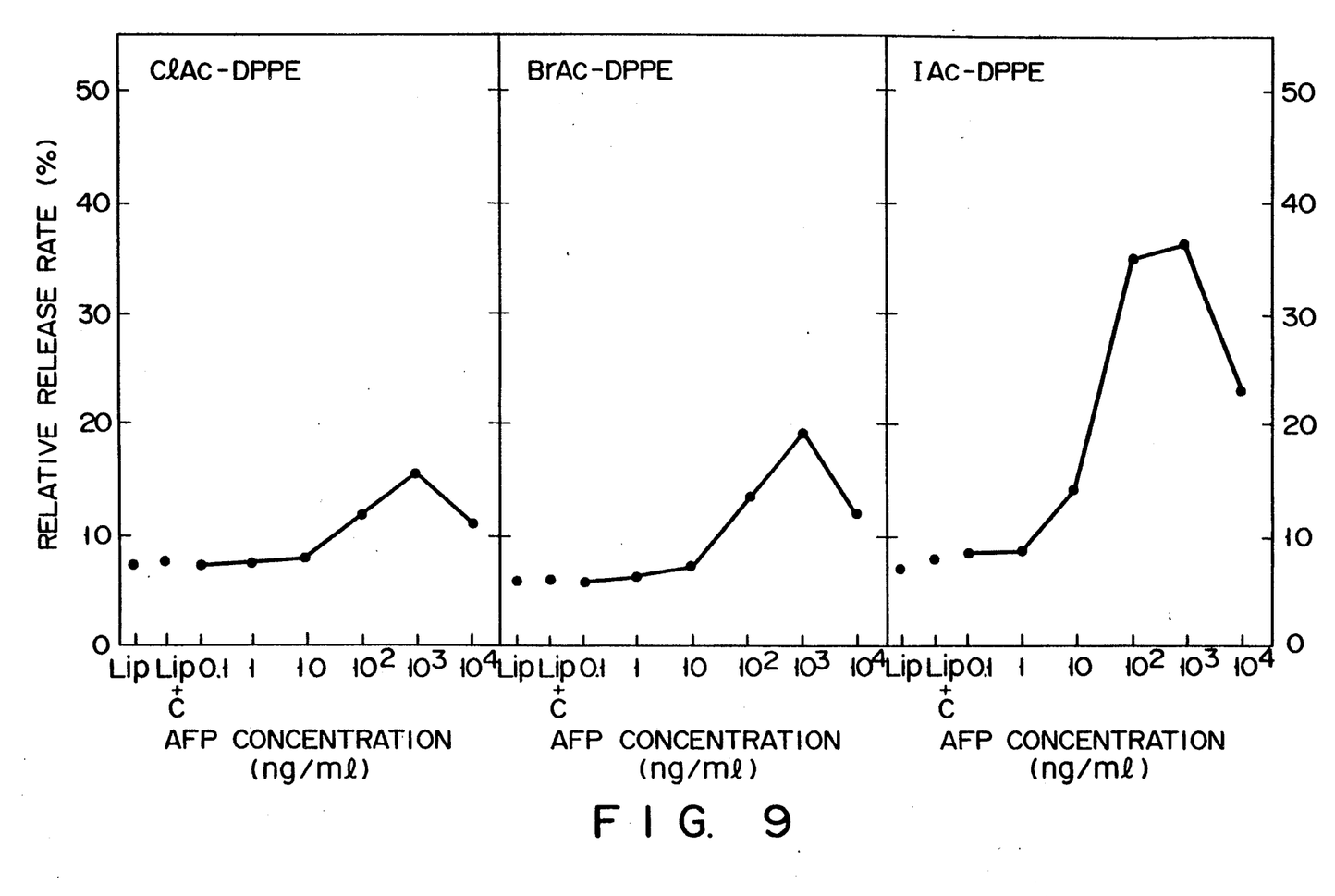
FIG. 9 is a graph showing a relative release rate of the CF obtained when a monoclonal antibody-immobilized liposome containing ClAc-DPPE, BrAc-DPPE, or IAc-DPPE is mixed with a human AFP solution.

Following the same procedures as in (5), each monoclonal antibody-immobilized liposome suspension and the human AFP solution having a predetermined concentration were mixed and reacted each other. Thereafter, 25 μl of a rabbit anti-human AFP antibody solution diluted by a factor of 50 and 25 μl of a complement solution diluted by a factor of 20 were added to the mixed solution and reacted with antigen-antibody complex. Then, the released CF amount in each case of the human AFP solutions was measured following the same procedures as in Example 1. Results are shown in FIG. 9. Note that in FIG. 9, Lip on the abscissa was a value obtained when only the liposome suspension was used, and Lip+C. thereon was a value obtained when only the complement solution was added to the liposome suspension. As is apparent from FIG. 9, every liposome exhibited a good response to the human AFP. Note that the response is better in an order of Cl<Br<I.

(7) Reaction with Proper Serum

The above monoclonal antibody-immobilized liposome (functional lipid was BrAc-DPPE) and 10 specimens of proper serum diluted by a factor of 10 by adding GVB+ were mixed respectively. 25 μl of a complement solution diluted by a factor of 20 were added to the resultant solution and reacted at 37° C. for 30 minutes. Relative release rates in this case are shown in Table 1. Note that Reference Example 3 in Table 1 indicates the result when a monoclonal antibody-immobilized liposome (functional lipid was DTP-DPPE) disclosed in Japanese Patent Application No. 58-224509 was used.

TABLE 1

| Sample | Relative Release Rate (%) | |
|---|---|---|
| | Example 2 | Reference Example 3 |
| 1 | 3 | 15 |
| 2 | 4 | 25 |
| 3 | 3 | 30 |
| 4 | 2 | 10 |
| 5 | 4 | 20 |
| 6 | 5 | 45 |
| 7 | 3 | 30 |
| 8 | 3 | 20 |
| 9 | 3 | 10 |
| 10 | 4 | 8 |

As is apparent from Table 1, the monoclonal antibody-immobilized liposome of this example has high stability in serum and superior characteristics to those of a conventional monoclonal antibody-immobilized liposome.

REFERENCE EXAMPLE 4

Figure 10:
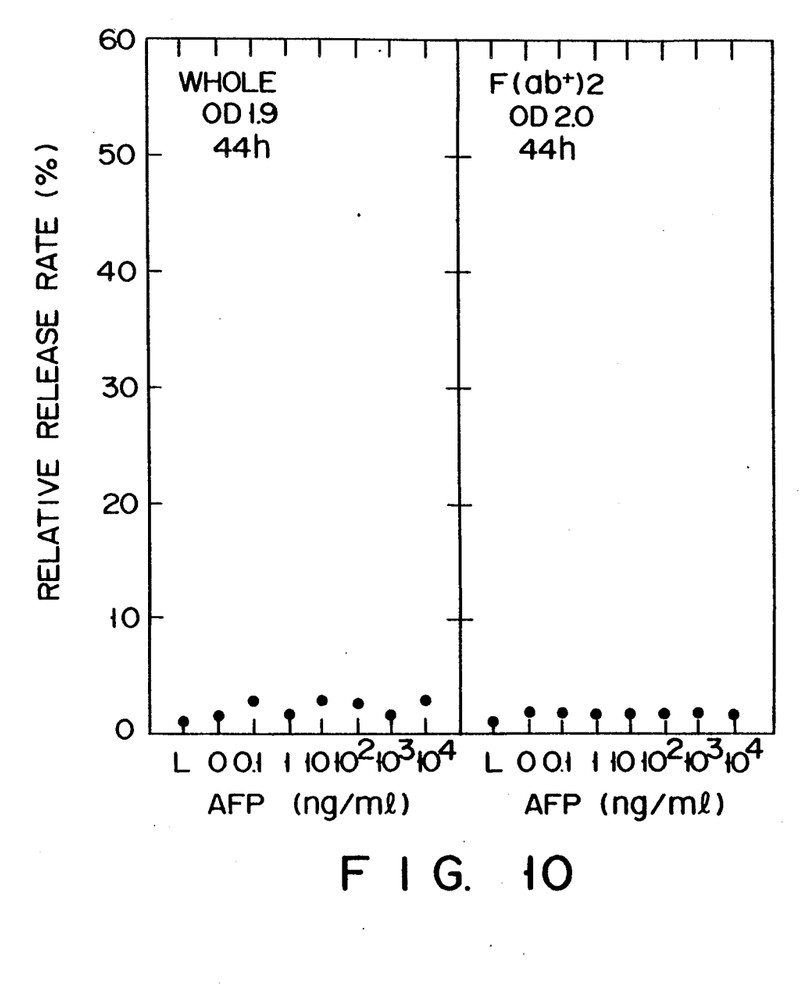
FIG. 10 is a graph showing a relative release rate of the CF obtained when a liposome reagent prepared in Reference Example 3 is mixed with a human AFP solution.

Reaction between Liposome having Monoclonal Antibody (Whole or F(ab')₂) immobilized thereto and Human AFP, The Monoclonal Antibody not having Free SH Group Following the same procedures as in Example 2, nonreduced monoclonal antibodies (Whole or F(ab')₂) were reacted with a liposome, and a response to the human AFP was measured. Results are shown in FIG. 10. As is apparent from FIG. 10, the liposome to which the Whole or F(at')₂ antibodies were immobilized did not respond to the human AFP at all.

EXAMPLE 3

(1) Preparation of Functional Lipid and Liposome

Following the same procedures as in Example 2, a functional lipid was prepared using bromoacetic acid as a halogenated acetic acid. Following the same procedures as in Example 2, a liposome suspension was prepared using the obtained functional lipid. A small amount of a 0.01 M HEPES buffer (containing 0.85% NaCl, pH 7.45) was added to the obtained liposome suspension, and then all the material was transferred to a centrifugal tube and repeatedly centrifuged at 4° C. and 15000 rpm for 20 minutes several times. Finally, the buffer was removed to obtain a pellet of the liposome.

(2) Modification of Monoclonal Antibody

A protein fraction (Fab') containing a free SH group was fractionated (1 ml each) from a monoclonal anti-human AFP antibody following the same procedures as in Example 2 except that a buffer having a predetermined pH within the range of 6 to 12 was used as a solvent for gel filtration performed by using Sephadex G-25.

(3) Immobilization of Monoclonal Antibody to Liposome

The pellet of liposome obtained in (1) and each 1 ml of the Fab' fractions obtained in (2) was mixed respectively and reacted with each other under stirring at 20° C. for 44 hours. After the reaction, each mixture was washed three times with the GVB⁻ and then suspended in 2 ml of the GVB⁻ and preserved at 4° C.

Measurement of Human AFP by Using Monoclonal Antibody-Immobilized Liposome

Following the same procedures as in Example 2, the released CF amount was measured using the monoclonal antibody-immobilized liposomes prepared at various pH conditions in (3) by the MTP-32 fluorospectrophotometer. The relative release rate was obtained on the basis of measurement value of fluorescence intensity and in accordance with the equation described above. Table 2 shows ranges of measurable concentration and relative release rates of the liposomes obtained when the monoclonal antibody-immobilized liposomes prepared by using the buffer having the respective pH values as solvent for gel filtration were used.

TABLE 2

| pH | Range of Measurable Concentration of AFP (ng/ml) | Relative Release Rate of Liposome (%) |
|---|---|---|
| 6 | 10 to 10³ | 15 |
| 7 | 1.0 to 10³ | 35 |
| 7.4 | 1.0 to 10³ | 45 |
| 8 | 1.0 to 10³ | 52 |
| 9 | 1.0 to 10³ | 55 |
| 10 | 1.0 to 10³ | 55 |
| 11 | 1.0 to 10³ | 50 |
| 12 | — | — |

In Table 2, the relative release rate of the liposome is increased as the pH increases within the pH range of 6 to 8 and is maintained substantially constant within the pH range of 8 to 11. As is apparent from Table 2, immobilization of the monoclonal antibody to the liposome is preferably performed at a pH of 7 to 11. When a liposome to which an antibody is immobilized within this pH range is used, immunoassay can be performed with higher measurement accuracy and a wider range of measurable concentration.

EXAMPLE 4

Following the same procedures as in Example 2, an interaction between a liposome and human serum was examined.

First, 50 specimens of human serum were divided into two groups, and one of the groups was diluted by a factor of 10 by adding the GVB+. Meanwhile, a monoclonal antibody-immobilized liposome which is suffered an immobilization at pH 8 was diluted by a factor of 10 by adding GVB+. 10 μl of the diluted liposome suspension was mixed with each 10 μl of the diluted serum solutions respectively and incubated at 37° C. for 10 minutes. Then, 25 μl of the GVB+ and 25 μl of a complement solution diluted by a factor of 20 were added to each resultant solution and reacted at 37° C. for 30 minutes.

50 human serum specimens of the other group were heated at 56° C. for 30 minutes and reacted in the same manner as described above.

Following the same procedures as in Example 2, a relative release rate was obtained for each specimen. Results are shown in FIG. 11.

Figure 12:
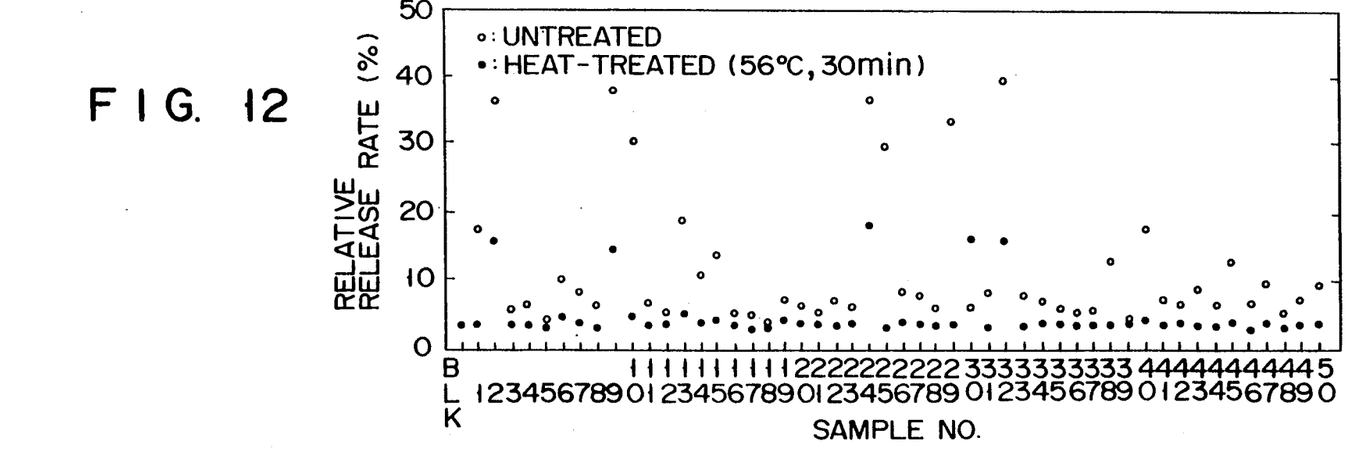
FIG. 12 is a graph showing a relative release rate of the CF obtained when the same human serum as used in FIG. 11 is mixed with a liposome having a monoclonal anti-human AFP antibody immobilized on the surface thereof through a disulfide bond by a conventional method.

For the purpose of comparison, following the same procedures as described above, the interaction between a liposome to which a monoclonal anti-human AFP antibody was immobilized through a disulfide bond by a conventional method and the human sera (50 specimens) were examined. Results are shown in FIG. 12.

Figure 11:
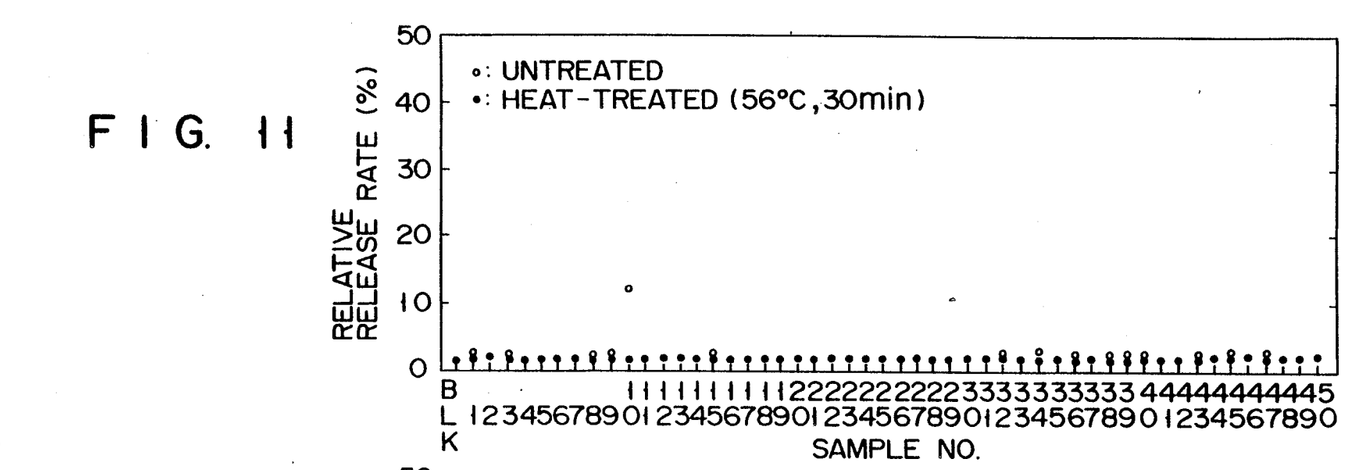
FIG. 11 is a graph showing a relative release rate of the CF obtained when human serum is mixed with a monoclonal antibody-immobilized liposome prepared using the lipid of the present invention in Example 4.

As is apparent from FIG. 11, the liposome of the present invention was very stable in the human sera. Note that although nonspecific lysis was found in one specimen, it is eliminated by heating the serum. However, as is apparent from FIG. 12, the conventional liposome was very unstable in the human sera.

What is claimed is:

1. a modified lipid compound represented by the following formula (I):

$$R-Y-(CH_2)_n-X \ldots \qquad (I)$$

wherein X is a halogen atom, Y is a member selected from the group consisting of —NHCO— and —COO—, R is a phospholipid or glycolipid residue, and n is 1.

2. A compound according to claim 1, wherein R is a phospholipid residue.

3. A compound according to claim 1, wherein R is an amino group-containing lipid residue.

4. A compound according to claim 3, wherein R is a phosphatidyl ethanolamine residue, and X is a member selected from the group consisting of Cl, Br, and I.

5. A lipid composition for immobilizing a bioactive substance, comprising one or more lipids at least one of which is a modified phospholipid or glycolipid compound represented by the following formula (I):

$$R-Y-(CH_2)_n-X \ldots \qquad (I)$$

wherein X is a halogen atom, Y is a member selected from the group consisting of —NHCO— and —COO—, R is a lipid residue, and n is 1.

6. A composition according to claim 5, wherein R is a phospholipid residue.

7. A composition according to claim 5, wherein R is an amino group-containing lipid residue.

8. A composition according to claim 7, wherein R is a phosphatidyl ethanolamine residue, and X is a member selected from the group consisting of Cl, Br, and I.

9. A composition according to claim 5, containing cholesterol and/or phosphatidyl choline.

10. A composition according to claim 5, containing cholesterol and diphalmitoylphosphatidyl choline.

* * * * *